United States Patent [19]

Mikami et al.

[11] Patent Number: 5,084,473
[45] Date of Patent: Jan. 28, 1992

[54] METHOD FOR PREVENTING OR TREATING RENAL FAILURE

[75] Inventors: Hiroki Mikami; Kazuharu Ienaga, both of Hyogo, Japan

[73] Assignee: Nippon Zoki Pharmaceutical Co., Ltd., Osaka, Japan

[21] Appl. No.: 564,520

[22] Filed: Aug. 9, 1990

[30] Foreign Application Priority Data

Aug. 9, 1989 [JP] Japan .................. 1-207699

[51] Int. Cl.$^5$ ............................. A61U 31/415
[52] U.S. Cl. ........................................ 514/390
[58] Field of Search ........................ 514/392, 390

[56] References Cited

U.S. PATENT DOCUMENTS

| 4,248,882 | 2/1981 | Sarges et al. | 424/273 R |
| 4,853,401 | 8/1989 | Bovy et al. | 514/389 |

*Primary Examiner*—Stanley J. Friedman
*Attorney, Agent, or Firm*—Armstrong, Nikaido, Masrmelstein, Kubovcik & Murray

[57] ABSTRACT

The present invention relates to a method for preventing or treating renal failure in a mannal which comprises administering the mammal an effective amount for renal failure of at least one hydantoin derivative of the following formula (I) or a pharmaeutically acceptable salt thereof.

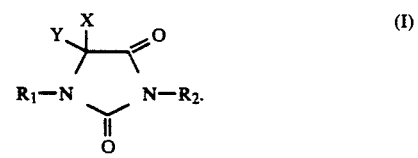

7 Claims, No Drawings

METHOD FOR PREVENTING OR TREATING RENAL FAILURE

BACKGROUND OF THE INVENTION

The present invention relates to a method for preventing or treating renal failure in a mammal which comprises administering the mammal an effective amount of at least one hydantoin derivative or a pharmaceutically acceptable salt thereof.

Since the number of renal failure patients treated with hemodialysis is increasing, great efforts have been given to the prevention, early detection and treatment of renal failure, the suppression of progression of renal failure, and the provision and spread of medical care of dialysis and renal transplantation. Several diseases, for example, various nephropathy such as diabetic nephropathy, nephrosclerosis, collagen disease and obstructive uropathy cause an obstruction of renal functions, and the patients fall into chronic renal failure. In renal failure, quantitative and qualitative homeostasis of body fluid composition can not be maintained, and it has been suggested that uremic toxins, which are not excreted and are accumulated in the body, cause obstructions and abnormalities of tissues, neuronal and metabolic systems. It is the present situation that there are not any suitable drugs for treating renal failure. Therefore, the developments of good drugs for renal failure are desired, for example, drugs which suppress the production of uremic toxins causing uremic symptoms. It has now been found that certain hydantoin derivatives have suppressing effect on the production of uremic toxins and improving effect on renal functions as well as low toxicity and great safety. As disclosed in Japan Kokai Tokkyo Koho JP 1986-122275, 1987-14 and 1987-45525, it was known that the hydantoin derivatives of the present invention had pharmacological effects such as hypoglycemic and hypolipidemic effects. However, therapeutic effect for renal failure of the said compounds was not known at all.

An object of the present invention is to provide a method for preventing or treating renal failure in a mammal which comprises administering the mammal an effective amount of at least one hydantoin derivative or a pharmaceutically acceptable salt thereof.

DETAILED DESCRIPTION OF THE INVENTION

The present invention relates to a method for preventing or treating renal failure in a mammal which comprises administering the mammal an effective amount of at least one hydantoin derivative of the following formula (I) or a pharmaceutically acceptable salt thereof:

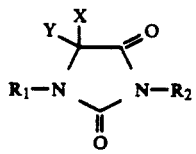

(I)

wherein each of $R_1$ and $R_2$, which may be the same or different, represents hydrogen, an alkyl group or a cycloalkyl group, and each of X and Y, which may be the same or different, represents hydrogen, hydroxy, an alkyl group or an alkoxy group, or X and Y together represent oxo group.

In the formula (I), each of $R_1$ and $R_2$, which may be the same or different, represents hydrogen; an alkyl group, preferably a straight or branched alkyl group having 1 to 20 carbon atoms such as methyl, ethyl, propyl, isopropyl, butyl, isobutyl, sec-butyl, tert-butyl, pentyl, isopentyl, neopentyl, tert-pentyl, hexyl, dimethylbutyl, heptyl, octyl, nonyl, decyl or stearyl; or a cycloalkyl group, preferably a cycloalkyl group having 3 to 8 carbon atoms such as cyclopropyl, cyclobutyl, cyclopentyl, cyclohexyl, cycloheptyl or cyclooctyl.

Each of X and Y, which may be the same or different, represents hydrogen; hydroxy; an alkyl group, preferably a straight or branched alkyl group having 1 to 3 carbon atoms such as methyl, ethyl, propyl or isopropyl; an alkoxy group, preferably a straight or branched alkoxy group having 1 to 5 carbon atoms such as methoxy, ethoxy, propoxy, isopropoxy, butoxy, isobutoxy, sec-butoxy, tert-butoxy, pentoxy, isopentoxy, neopentoxy; or X and Y together represent oxo group.

Preferred compounds of the present invention are indicated as follows:

| No. | Name |
|---|---|
| 1 | 1-methylhydantoin |
| 2 | 3-methylhydantoin |
| 3 | 1-ethylhydantoin |
| 4 | 1-butylhydantoin |
| 5 | 1,5-dimethylhydantoin |
| 6 | 3,5-dimethylhydantoin |
| 7 | 1-hexylhydantoin |
| 8 | 1-decylhydantoin |
| 9 | 1-stearylhydantoin |
| 10 | 1-cyclopentylhydantoin |
| 11 | 1-cyclohexylhydantoin |
| 12 | 1-(1,3-dimethylbutyl)hydantoin |
| 13 | 1-tert-butylhydantoin |
| 14 | 1,3-dicyclohexylhydantoin |
| 15 | 3-cyclohexylhydantoin |
| 16 | 1-cyclohexyl-3-methylhydantoin |
| 17 | 1,3-dimethylhydantoin |
| 18 | 5-hydroxy-1-methylhydantoin |
| 19 | 5-hydroxy-3-methylhydantoin |
| 20 | 5-hydroxy-1-ethylhydantoin |
| 21 | 5-hydroxy-1-butylhydantoin |
| 22 | 5-methoxy-1-methylhydantoin |
| 23 | 5-butoxy-3-methylhydantoin |
| 24 | 5-ethoxy-1-methylhydantoin |
| 25 | 5-methoxy-3-methylhydantoin |
| 26 | 5-methoxy-1-cyclohexylhydantoin |
| 27 | 5-hydroxy-1,5-dimethylhydantoin |
| 28 | 5-hydroxy-3,5-dimethylhydantoin |
| 29 | 5-hydroxy-1-hexylhydantoin |
| 30 | 5-hydroxy-1-decylhydantoin |
| 31 | 5-hydroxy-1-stearylhydantoin |
| 32 | 5-hydroxy-1-cyclopentylhydantoin |
| 33 | 5-hydroxy-1-cyclohexylhydantoin |
| 34 | 5-hydroxy-1-(1,3-dimethylbutyl)hydantoin |
| 35 | 5-hydroxy-1-tert-butylhydantoin |
| 36 | 5-hydroxy-1,3-dicyclohexylhydantoin |
| 37 | 5-methoxy-3-cyclohexylhydantoin |
| 38 | 5-hydroxy-1-cyclohexyl-3-methylhydantoin |
| 39 | 5-hydroxy-1,3-dimethylhydantoin |
| 40 | imidazolidinetrione |
| 41 | 1-methylimidazolidinetrione |
| 42 | 1-ethylimidazolidinetrione |
| 43 | 1-butylimidazolidinetrione |
| 44 | 1-isobutylimidazolidinetrione |
| 45 | 1-tert-butylimidazolidinetrione |
| 46 | 1-hexylimidazolidinetrione |
| 47 | 1-(1,3-dimethylbutyl)imidazolidinetrione |
| 48 | 1-decylimidazolidinetrione |
| 49 | 1-cyclopentylimidazolidinetrione |
| 50 | 1-cyclohexylimidazolidinetrione |
| 51 | 1,3-dimethylimidazolidinetrione |
| 52 | 1-cyclopentyl-3-ethylimidazolidinetrione |

-continued

| No. | Name |
|---|---|
| 53 | 1,3-dicyclohexylimidazolidinetrione |

The hydantoin derivatives of the present invention include pharmaceutically acceptable salts of the compounds having formula (I) above, for example, salts as acid addition with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, glyconic acid, lactic acid, malonic acid, fumaric acid, anthranilic acid, benzoic acid, cinnamic acid, p-toluenesulfonic acid, naphthalenesulfonic acid or sulfanilic acid, salts with alkali metal such as sodium or potassium, salts with alkaline-earth metal such as calcium, magnesium or barium, or salts with other metals such as aluminum.

The hydantoin derivatives of this invention may also include their metal complexes, for example, complexes with zinc, nickel, cobalt, copper, iron etc.

These salts and metal complexes can be produced from free hydantoin derivatives in the usual way or can be interchanged with each other.

When optical isomers exist in the compounds of the invention, the present invention includes any of the d-, l- and dl-isomers.

The hydantoin derivatives of the present invention and a process for manufacturing them are disclosed in Japan Kokai Tokkyo Koho JP 1986-122275, 1987-14 and the like.

The following descriptions serve to illustrative pharmacological studies of the compounds of the present invention.

(1) Improving Effect on Renal Function

The improving effect on renal function was investigated in rats with chronic renal failure induced by an adenine diet. Adenine-induced chronic renal failure rats were prepared according to the method by Yokozawa et al. [Nephron 51(3), 388-392 (1989)]. Namely, by continuous administration of 0.75% adenine diet for two to five weeks, azotemia, an abnormal urea cycle, abnormal pattern of free amino acids in the blood and abnormal metabolism of electrolyte were observed together with renal histological changes.

These biochemical findings in adenine-fed rats bear close resemblance to metabolic abnormalities in human chronic renal failure. Therefore, the adenine-induced chronic renal failure rats is a suitable experimental model which is useful to study chronic renal failure. The compounds of the present invention were orally administered, which was started at the same time as beginning of adenine administration.

In order to evaluate the efficacy of the test compounds, with renal histological observation, blood urea nitrogen (BUN), phosphate (P) and calcium (Ca) in serum, and uremic toxins such as methylguanidine (MG), creatinine (Cr), guanidinosuccinic acid (GSA) and the like in serum, urine, kidney, liver and muscle were determined by the methods disclosed in the said literature Yokozawa et al. Particularly, we focused methylguanidine, which was regarded as the most important uremic toxin, to study the improving effect on renal function of the compounds of the present invention.

Compound 18 was administered for 24 days (250 mg/kg/day), and the results are shown in Table 1 to 3. Asterisks indicate significant differences (*: $p<0.05$, : $p<0.01$, *: $p<0.001$) from the control.

TABLE 1

| [Serum] | Control | Test compound |
|---|---|---|
| BUN (mg/dl) | 107.4 ± 11.1 | 71.3 ± 6.7* |
| Cr (mg/dl) | 35.5 ± 2.5 | 24.4 ± 1.5** |
| MG (μg/dl) | 7.3 ± 1.3 | 1.7 ± 0.3*** |
| GSA (μg/dl) | 115.4 ± 15.0 | 22.9 ± 1.1*** |
| P (mg/dl) | 14.9 ± 1.2 | 11.0 ± 0.9* |
| Ca (mg/dl) | 7.4 ± 0.5 | 9.5 ± 0.5* |

TABLE 2

| [Urine] | Control | Test compound |
|---|---|---|
| Urea (mg/day) | 247.3 ± 27.3 | 353.9 ± 38.3* |
| MG (μg/day) | 51.5 ± 4.6 | 25.7 ± 3.0*** |
| GSA (μg/day) | 112.0 ± 13.6 | 83.8 ± 7.6 |

TABLE 3

| [MG (μg/g of tissue)] | Control | Test compound |
|---|---|---|
| Liver | 0.188 ± 0.030 | Not determined |
| Kidney | 0.406 ± 0.145 | 0.239 ± 0.032 |
| Muscle | 0.316 ± 0.053 | 0.148 ± 0.009* |

In the same manner, the results in the tests using Compound 1 (150 mg/kg/day for 25 days) and Compound 41 (250 mg/kg/day for 14 days) are shown in Table 4.

TABLE 4

| | [MG (μg/urine for 6 hrs)] | |
|---|---|---|
| | Control | Test compound |
| Compound 1 | 9.8 ± 2.4 | 6.0 ± 1.9* |
| Compound 41 | 4.5 ± 0.7 | 2.3 ± 0.3** |

According to the pathological observations, histological changes to morbid state at kidney of the rat, to which the compounds of the present invention were administered, were apparently inhibited as compared with the adenine-induced chronic renal failure rats.

As clearly shown by the above-mentioned results, the hydantoin derivatives of the present invention have the normalizing effect on renal functions falling into morbid state. Namely, the compounds of this invention significantly lower the high levels of urea nitrogen and phosphate in serum, and also raise the low level of serum calcium and increase the excretion of urea into urine.

The results in Tables 1 to 4 show that the compounds of the invention have the pharmacological effect lowering the abnormal high levels of uremic toxins such as methylguanidine, creatinine, guanidinosuccinic acid and urea in serum, urine and the like down to the normal level. Suppressive effect on the production of uremic toxins is one of the mechanisms of normalizing effect on renal functions of the compounds of the present invention.

The hydantoin derivatives of the present invention significantly suppress the production of uremic toxins causing uremia symptoms and have an excellent improving effect on renal functions. Therefore, they are useful as preventive medicine or remedy for chronic renal failure caused by various nephropathy such as diabetic nephropathy, nephrosclerosis, collagen disease or obstructive uropathy, and its complicated uremic syndrome, such as neuropathy, metabolic and endocrinic disorders. Also the compounds of the present invention are useful as drugs improving renal functions which are damaged by the side effects of antineoplastics such as cisplatin, methotrexate and the like. Since the compounds of the invention have low toxicity and great safety, its long-term continuous administration and oral use are possible, so that they can be advantageously used especially in the treatment of the said chronic diseases.

The compounds of the present invention can be made into pharmaceutical compositions by combination with appropriate medicinal carriers or diluents, and can be formulated into preparations in solid, semisolid, liquid or gaseous form in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or non-aqueous solvent, such as distilled water for injection, physiologically saline solution, vegetable oil, synthetic aliphatic acid glycerides, esters of higher aliphatic acid or propylene glycol.

Furthermore, according to a kind of disease or patient, the compounds of the invention can be formulated into other preparations suitable for treatment of the disease, such as emulsion, syrup, inhalation, aerosol, collyrium, ointment and cataplasma.

The desirable dose of the compounds of the present invention varies with the subject, form of the drug, method and period of administration. However, in order to obtain desirable effects, generally it is recommended to administer orally 1 to 1,000 mg, preferably 5 to 600 mg daily. Unit preparations are also recommended for administration in one to several units daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

Prescription Example 1 (Tablet)

| Component | Content in a tablet (mg) |
| --- | --- |
| compound of this invention | 100 |
| lactose | 100 |
| crystalline cellulose | 40 |
| calcium carboxymethylcellulose | 20 |
| magnesium stearate | 10 |
| Total | 270 mg |

Prescription Example 2 (Capsule)

| Component | Content in a capsule (mg) |
| --- | --- |
| compound of this invention | 50 |
| lactose | 250 |
| Total | 300 mg |

Prescription Example 3 (Injection)

| Component | Content in an ampule (mg) |
| --- | --- |
| compound of this invention | 10 |
| sodium chloride | proper amount |
| distilled water for injection | proper amount |
| Total | 1 ml |

We claim:

1. A method for improving renal function in a mammal which comprises administering to the mammal an amount effective to improve renal function of at least one hydantoin compound of the formula (I):

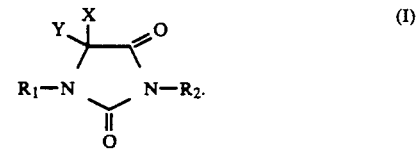

wherein each of $R_1$ and $R_2$, which may be the same or different, represents hydrogen, an alkyl group or a cycloalkyl group, and each of X and Y, which may be the same or different, represents hydrogen, hydroxy, an alkyl group or an alkoxy group, or X and Y together represent an oxo group;

or a pharmaceutically acceptable salt thereof.

2. A method according to claim 1 wherein X and Y are hydrogens.

3. A method according to claim 2 wherein $R_2$ is hydrogen and $R_1$ is an alkyl group.

4. A method according to claim 1 wherein X is hydrogen and Y is hydroxy.

5. A method according to claim 4 wherein $R_2$ is hydrogen and $R_1$ is an alkyl group.

6. A method according to claim 1 wherein X and Y together represent an oxo group.

7. A method according to claim 6 wherein $R_2$ is hydrogen and $R_1$ is an alkyl group.

* * * * *